United States Patent
Scheffler et al.

(10) Patent No.: US 7,166,564 B2
(45) Date of Patent: Jan. 23, 2007

(54) OPTICAL BRIGHTENERS

(75) Inventors: Goetz Scheffler, Grenzach-Wyhlen (DE); Hauke Rohwer, Lörrach (DE); René Schlatter, Basel (CH); Robert Hochberg, Merzhausen (DE)

(73) Assignee: Ciba Specialty Chemicals Corp., Tarrytown, NY (US)

(*) Notice: Subject to any disclaimer, the term of this patent is extended or adjusted under 35 U.S.C. 154(b) by 0 days.

(21) Appl. No.: 10/568,638

(22) PCT Filed: Aug. 11, 2004

(86) PCT No.: PCT/EP2004/051767

§ 371 (c)(1),
(2), (4) Date: Feb. 16, 2006

(87) PCT Pub. No.: WO2005/019189

PCT Pub. Date: Mar. 3, 2005

(65) Prior Publication Data

US 2006/0197060 A1    Sep. 7, 2006

(30) Foreign Application Priority Data

Aug. 21, 2003  (EP) ................................ 03102616

(51) Int. Cl.
C11D 3/30     (2006.01)
C07D 251/48   (2006.01)

(52) U.S. Cl. .................................. 510/394; 544/193.2
(58) Field of Classification Search ................ None
See application file for complete search history.

(56) References Cited

U.S. PATENT DOCUMENTS

| | | | |
|---|---|---|---|
| 3,663,538 A | 5/1972 | Lebkücher et al. | 260/240 |
| 5,945,396 A | 8/1999 | Eckhardt et al. | 510/521 |
| 6,143,889 A | 11/2000 | Metzger et al. | 544/193.2 |
| 6,482,241 B1 | 11/2002 | Metzger et al. | 8/115.51 |
| 6,723,846 B1 | 4/2004 | Metzger et al. | 544/193.2 |
| 2004/0063706 A1 | 4/2004 | Metzger et al. | 514/241 |
| 2005/0106114 A1 | 5/2005 | Metzger et al. | 424/59 |
| 2005/0120490 A1 | 6/2005 | Metzger et al. | 8/115.51 |
| 2006/0048309 A1 | 3/2006 | Donze et al. | 8/549 |

FOREIGN PATENT DOCUMENTS

| | | | |
|---|---|---|---|
| DE | 1955431 | * | 11/1969 |
| GB | 616523 | * | 1/1949 |
| GB | 751997 | * | 7/1956 |

\* cited by examiner

*Primary Examiner*—John R. Hardee
(74) *Attorney, Agent, or Firm*—Tyler A. Stevenson

(57) ABSTRACT

The invention relates to novel bis(triazinylamino)stilbenes which are suitable as UV absorbers and fluorescent whiteners for textile materials and also bring about an increase in the treated textile material.

13 Claims, No Drawings

OPTICAL BRIGHTENERS

The present invention relates to novel stilbene derivatives, to a process for the preparation of such compounds and to their use in the optical brightening of textile fibres and paper.

Sulfonic acid derivatives of bis(triazinylamino)stilbenes are among the most commonly used optical brighteners for paper and textiles.

Cationic bis(triazinylamino)stilbenes are frequently used in liquid detergents on account of their compatibility with cationic ingredients. The known cationic stilbene derivatives can be used only to a limited extent, however, in the field of textiles on account of their low substantivity for cellulose.

It has now been found that certain amphoteric or cationic bis(triazinylamino)stilbenes exhibit a high brightener action both in paper manufacture and in textile finishing and when used in detergents. The novel compounds exhibit strong absorption in both the UV-A and the UV-B range and have a high degree of substantivity for cellulose.

The present invention relates to compounds of formula (1), (2) or (3)

wherein
M is hydrogen, an alkali metal ion or an ammonium ion,
$A_1$ is —$OR_1$, —$NHR_1$, N-morpholinyl or 1-piperidyl,
$A_2$ is —$OR_2$, —$NHR_2$, N-morpholinyl or 1-piperidyl,
$E_1$, $E_2$, $E_3$ and $E_4$ are each independently of the others —O—, —NH— or —$NR_9$—, wherein $R_9$ together with $R_4$, $R_6$, $R_2$ or $R_{12}$ forms an ethylene radical,
$R_1$ to $R_6$, $R_{11}$ and $R_{12}$ are each independently of the others hydrogen, alkyl, alkoxy, aryl, aralkyl, alkoxyalkyl, hydroxyalkyl, aminoalkyl or a group of the formula —$(C_nH_{2n}Y)_m$—$R_7$, wherein Y is —O—, —NH—, —$NR_8$—, —CONH— or —$CONR_8$—, $R_7$ is hydrogen, alkyl or aryl and $R_8$ is alkyl or aryl, n is a number from 2 to 6 and m is a number from 1 to 10, or pairs of two radicals $R_1$ and $R_2$, $R_3$ and $R_4$, $R_5$ and $R_6$ or $R_{11}$ and $R_{12}$ together form a bivalent radical of the formula —$CH_2CH_2OCH_2CH_2$— or, when $E_1$, $E_2$, $E_3$ or $E_4$ is —$NR_9$—,
$R_4$, $R_6$, $R_2$ or $R_{12}$ together with $R_9$ forms an ethylene radical,
$R_{10}$, $R_{13}$, $R_{14}$ and $R_{15}$ are each independently of the others alkyl, alkenyl, aryl or aralkyl,

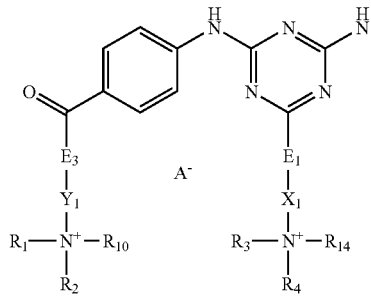

(1)

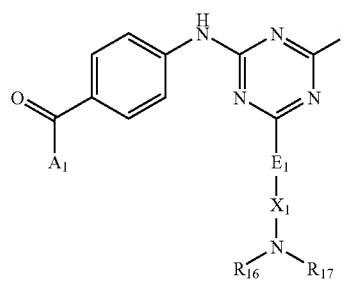

(2)

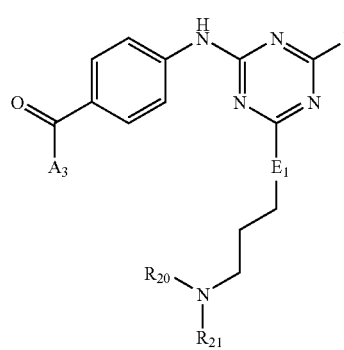

(3)

X₁ and X₂ are each independently of the other 1,2-cyclohexanediyl, a group of the formula —($C_nH_{2n}$)ₘ— or a group of the formula —($C_nH_{2n}Y$)ₘ—, wherein Y is —O—, —NH—, —NR₈—, —CONH— or —CONR₈— and R₈ is alkyl or aryl, n is a number from 2 to 6 and m is a number from 1 to 10, Y₁ and Y₂ are each independently of the other 1,2-cyclohexanediyl, a group of the formula —($C_nH_{2n}$)ₘ— or a group of the formula —($C_nH_{2n}Y$)ₘ—, wherein Y is —O—, —NH—, —NR₈—, —CONH— or —CONR₈— and R₈ is alkyl or aryl, n is a number from 2 to 6 and m is a number from 1 to 10 and A⁻ is a singly charged anion or the two A⁻ form a doubly charged anion, R₁₆, R₁₇, R₁₈ and R₁₉ are each independently of the others hydrogen, 2-hydroxyethyl, 2-aminoethyl or 3-aminopropyl, R₂₀, R₂₁, R₂₂ and R₂₃ are each independently of the others alkyl, and A₃ and A₄ are 2-hydroxyethylamino, 3-dimethylaminopropylamino or 3-diethylaminopropylamino.

The amphoteric compounds of formulae (2) and (3) can be in the form of internal or external salts. For example, when M in formula (3) is hydrogen, the compound of formula (3) can be in the form of a mixture of the neutral compound and the zwitterion in equilibrium:

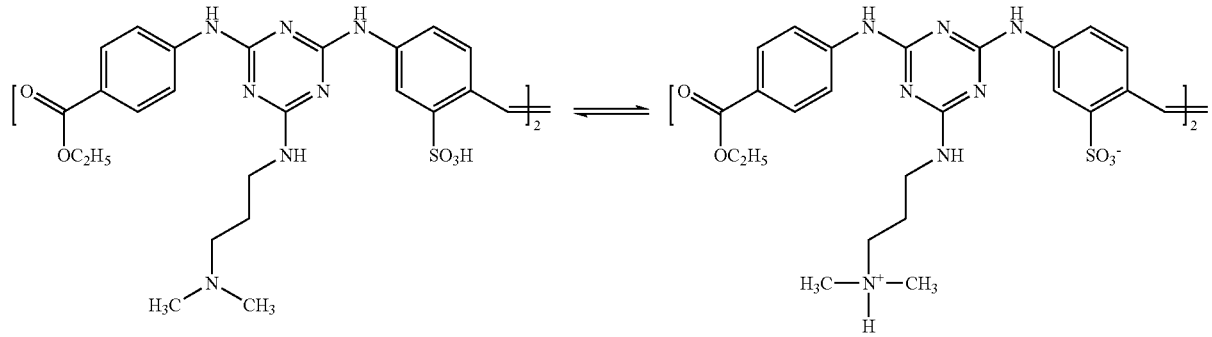

M in formula (2) and formula (3) can also be an alkali metal cation, such as Na⁺ or K⁺, or an unsubstituted or substituted ammonium ion, such as NH₄⁺ or N(CH₃)₄⁺.

When any radicals in formula (1), (2) or (3) are alkyl, such radicals are preferably straight-chain or branched C₁–C₁₂alkyl groups. Examples thereof are methyl, ethyl, propyl, isopropyl, n-butyl, isobutyl, sec-butyl, tert-butyl, amyl, tert-amyl (1,1-dimethylpropyl), 1,1,3,3-tetra-methylbutyl, hexyl, 2-methylpentyl, neopentyl, cyclopentyl, cyclohexyl and their respective isomers.

Alkoxy groups are preferably C₁–C₆alkoxy groups, for example methoxy, ethoxy, n-propoxy, isopropoxy, n-butoxy or tert-butoxy.

Aryl radicals in formula (1) or (2) are preferably unsubstituted or alkyl-substituted C₆–C₂₄aryl, for example phenyl, tolyl, mesityl and isityl.

Suitable aralkyl groups preferably contain 6–12 carbon atoms. Examples thereof are benzyl and 2-phenylethyl.

Suitable alkoxyalkyl groups are, for example, 2-methoxyethyl, 2-ethoxyethyl, 3-methoxy-propyl and 3-ethoxypropyl.

Examples of hydroxyalkyl are 2-hydroxyethyl, 3-hydroxypropyl, 2-hydroxypropyl, 4-hydroxy-butyl, 3-hydroxybutyl and 2-hydroxybutyl.

Examples of aminoalkyl are 2-aminoethyl, 3-aminopropyl, 2-aminopropyl, 4-aminobutyl, 3-aminobutyl and 2-aminobutyl.

Alkenyl groups as radicals R₁₀, R₁₃, R₁₄ or R₁₅ preferably contain 3–6 carbon atoms, for example allyl, buten-2-yl and penten-2-yl.

A⁻ in formula (1) is a colourless anion of an inorganic or organic acid. Examples of such anions are halide, such as chloride, bromide or iodide, sulfate, methyl sulfate, tetrafluoroborate, aminosulfonate, perchlorate, carbonate, hydrogen carbonate, benzenesulfonate, naphthalenesulfonate, 4-chlorobenzenesulfonate, oxalate, maleate, acetate, propionate, lactate, succinate, chloroacetate, tartrate, methanesulfonate and benzoate.

Preferred anions are hydrogen sulfate, sulfate, lactate, acetate and especially chloride and methyl sulfate.

In a preferred embodiment of the invention, the compounds of formulae (2) and (3) are symmetrical; that is to say preference is given to compounds of formula (2) wherein the substituents A₁ and A₂, E₁ and E₂, X₁ and X₂, R₁₆ and R₁₈ and also R₁₇ and R₁₉ are in each case identical; and compounds of formula (3) wherein the substituents A₃ and A₄, E₁ and E₂, R₂₀ and R₂₂ and also R₂₁ and R₂₃ are in each case identical.

Also preferred are compounds of formula (1) wherein the substituents E₁ and E₂, E₃ and E₄, X₁ and X₂, Y₁ and Y₂, R₃ and R₅, R₄ and R₆, R₁₄ and R₁₅, R₁ and R₁₁, R₂ and R₁₂ and also R₁₀ and R₁₃ are in each case identical.

In formulae (1) and (2), X₁ and X₂ are preferably ethylene or trimethylene.

In formula (3), R₂₀, R₂₁, R₂₂ and R₂₃ are preferably methyl or ethyl.

Also preferred are compounds of formula (2) or (3) wherein A₁, A₂, A₃ and A₄ are amino, methylamino, 2-hydroxyethylamino, 3-dimethylaminopropylamino or ethoxy.

Preference is also given to compounds of formula (1) wherein R₁ to R₆ and R₁₀ to R₁₅ are methyl.

The compounds of formulae (1), (2) and (3) according to the invention can be synthesised by known methods, starting from cyanuric chloride and 4,4'-diaminostilbene-2,2'-disulfonic acid.

The compounds of formula (2) can be prepared, for example, by reacting cyanuric chloride with, in any order, 4,4'-diaminostilbene-2,2'-disulfonic acid and compounds of formulae

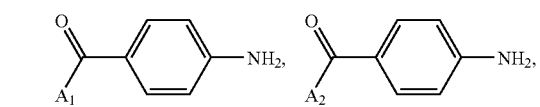

-continued

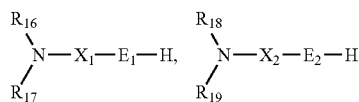

wherein $A_1$, $A_2$, $X_1$, $X_2$, $E_1$, $E_2$, $R_{16}$, $R_{17}$, $R_{18}$ and $R_{19}$ are as defined above.

The compounds of formula (1) can be synthesised analogously, for example by reacting cyanuric chloride first with 4,4'-diaminostilbene-2,2'-disulfonic acid and a compound of formula

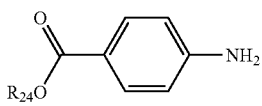

wherein $R_{24}$ is alkyl. The intermediate so obtained can then be reacted, as described e.g. in WO 02/055509, with compounds of formulae

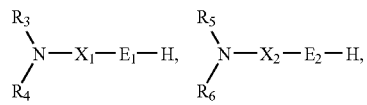

wherein $R_1$ to $R_6$, $R_{11}$, $R_{12}$, $E_1$ to $E_4$, $X_1$, $X_2$, $Y_1$ and $Y_2$ are as above, and then the basic N atoms are quaternised by known methods by reaction with compounds of formulae $R_{10}$-LG, $R_{13}$-LG, $R_{14}$-LG and $R_{15}$-LG, wherein $R_{10}$, $R_{13}$, $R_{14}$ and $R_{15}$ are as defined above and LG is a leaving group.

Suitable compounds of formulae $R_{10}$-LG, $R_{13}$-LG, $R_{14}$-LG and $R_{15}$-LG are inter alia the customary alkylating agents known to the person skilled in the art. Examples thereof are alkyl or allyl halides, such as methyl iodide or allyl chloride, dialkyl sulfates, such as dimethyl sulfate or diethyl sulfate, or sulfonic acid esters, such as methyl tosylate or methyl brosylate.

The starting compounds, the reaction conditions and the methods of separating and purifying the products are known to the person skilled in the art.

The invention relates also to a process for the preparation of symmetrical compounds of formula (2), which process comprises reacting cyanuric chloride by known methods with, in succession in any order, a compound of formula (4)

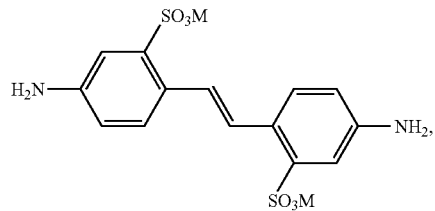

a compound of formula (5)

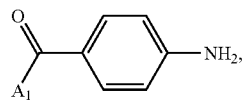

and a compound of formula (6)

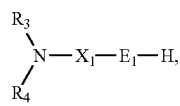

wherein M, $A_1$, $E_1$, $X_1$, $R_3$ and $R_4$ are as defined above.

The symmetrical compounds of formula (2) obtained by that process can readily be converted into symmetrical compounds of formula (1) by reaction with the corresponding amines and subsequent quaternisation.

The present invention relates also to a process for the preparation of symmetrical compounds of formula (3), which process comprises reacting cyanuric chloride by known methods with, in succession in any order, a compound of formula (4)

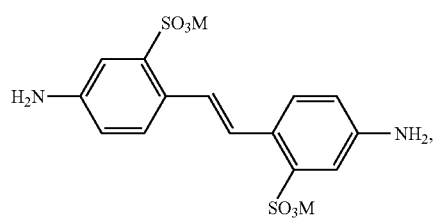

a compound of formula (7)

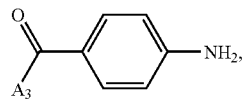

and a compound of formula (8)

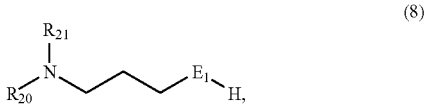

wherein M, $A_3$, $E_1$, $R_{20}$ and $R_{21}$ are as defined above.

A further aspect of the invention relates to a composition for brightening synthetic or natural organic materials, comprising water, a compound of formula (1), (2) or (3) and optionally further adjuvants.

Such brightener compositions preferably comprise water and, based on the total weight of the formulation, 3–25% by weight, especially 5–15% by weight, of a brightener of formula (1) or (2) and 0–60% by weight, especially 5–50% by weight, adjuvants.

Suitable adjuvants are, for example, anionic or non-ionic dispersants, such as ethylene oxide adducts of fatty alcohols, higher fatty acids, alkyl phenols, ethylenediamine-ethylene oxide/propylene oxide adducts, N-vinylpyrrolidone/3-vinylpropionic acid copolymers, water retention agents, such as ethylene glycol, glycerol or sorbitol, or biocides.

The compounds of formulae (1), (2) and (3) according to the invention are especially suitable for the optical brightening of natural, semi-synthetic or synthetic textile fibres or of paper.

The novel bis(triazinylamino)stilbenes are preferably used for the treatment of textile fibre materials, because, by virtue of their high absorption capacity in both the UV-A and the UV-B range, there is obtained not only an excellent brightener action but also a considerable increase in the sun-protection factor (SPF).

The invention therefore relates also to a method of increasing the SPF of a textile fibre material, which comprises treating the textile fibre material with 0.05–3.0% by weight, based on the weight of the textile fibre material, of one or more compounds of formula (1), (2) or (3).

The textile fibres which can be treated in accordance with the method of the invention can be natural or synthetic fibres and mixtures thereof. Examples of natural fibres are vegetable fibres, such as cotton, viscose, flax, rayon or linen, and animal fibres, such as wool, mohair, cashmere, angora and silk. Synthetic fibres are, for example, polyester, polyamide and polyacrylonitrile fibres. Preferred textile fibres are cotton, polyamide and wool fibres.

The textile fibres to be treated preferably have a density of less than 200 g/cm$^2$ and have not previously been dyed in dark shades.

Depending upon the compound of formula (1), (2) or (3) used, the treatment can advantageously be carried out in a neutral, acid or alkaline bath. The method is normally carried out in a temperature range of 20° C.–140° C., for example at or close to the boiling point of the aqueous bath, e.g. at about 90° C.

The application of the optical brighteners, optionally in combination with the application of dyes, can be carried out by conventional methods known from textile dyeing, for example the exhaust process or the pad-dyeing process.

When the method according to the invention is combined with a textile treatment or textile finishing process, such a combined treatment can advantageously be carried out using suitable stable preparations that comprise the compound of formula (1), (2) or (3) in a concentration such that the desired SPF improvement is achieved.

In certain cases, the compounds of formula (1), (2) or (3) can be rendered fully active by an after-treatment. Such an after-treatment may be a chemical treatment, such as treatment with an acid, a thermal treatment or a combined chemical/thermal treatment.

The compounds of formula (1), (2) or (3) can advantageously be used in admixture with an extender, such as anhydrous sodium sulfate, $Na_2SO_4.10H_2O$, NaCl, $Na_2CO_3$, an alkali metal phosphate, such as sodium or potassium orthophosphate, sodium or potassium pyrophosphate or sodium or potassium tripolyphosphate.

In addition to the compounds of formula (1), (2) or (3), the brightener mixtures according to the invention may comprise customary additives. Examples of such additives are emulsifiers, perfumes, colorants, opacifiers, further fluorescent whiteners, bactericides, non-ionic surfactants, fabric-care constituents, especially fabric conditioners, dirt-loosening or dirt-repellent constituents, water-proofing agents, anti-gelling agents, such as nitrites or nitrates of alkali metals, especially sodium nitrate, and corrosion inhibitors, such as sodium silicate.

The amount of each of those additives is preferably <2% and is especially in the range of 0.01–1.0%, based on the weight of the fibres being treated.

The treatment method according to the Invention can also be carried out by washing the textile fibre material with a detergent that comprises at least one compound of formula (1), (2) or (3).

The following Examples illustrate the invention.

I. PREPARATION EXAMPLES

I.1. Compound of Formula (100)

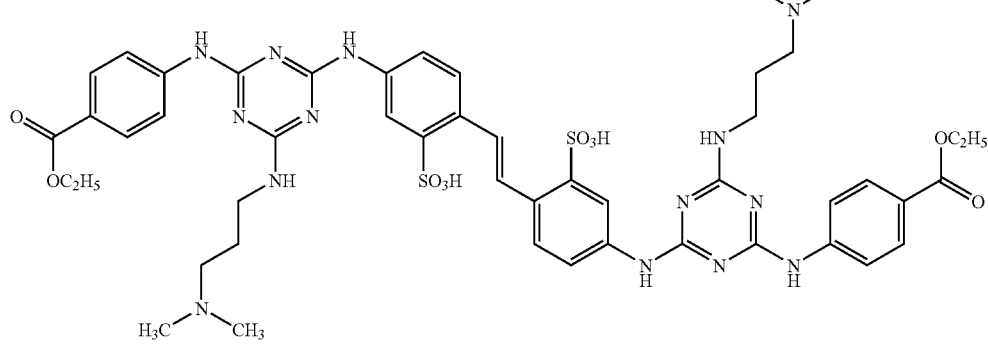

(a) Intermediate of Formula (100a)

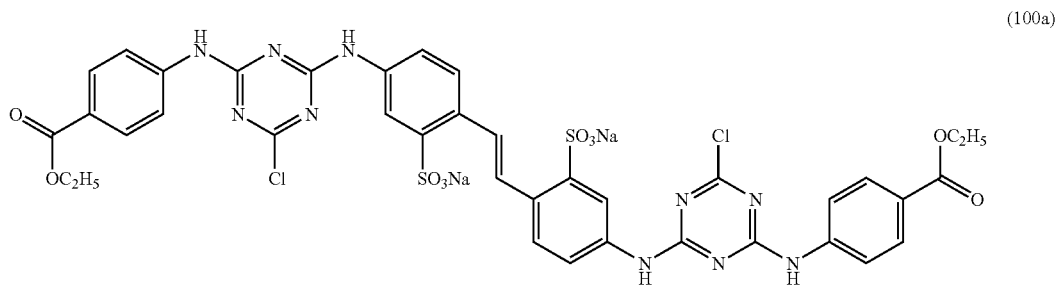

400 g of ice-water and 120 g (0.65 mol) of cyanuric chloride dissolved in 753 g of methyl ethyl ketone are introduced into a 2.5 liter flat-flanged flask. Then, in the course of 70 min, 990 ml of a 12% solution of 4,4′-diaminostilbene-2,2′-disulfonic acid in soda water are slowly added dropwise at pH 4.5–5.0 so that no excess of disulfonic acid is formed. When the addition is complete, stirring is carried out for 10 min at an internal temperature of 5–10° C. 107.3 g (0.65 mol) of 4-aminobenzoic acid ethyl ester are then introduced into the resulting yellow-brown suspension in the course of 10 min at 5–20° C. and pH 7.0–7.5.

The yellow suspension is heated to 72° C.; after half an hour, 11 ml of 50% NaOH and after a further half an hour 47 ml of 50% NaOH are added. After 1.5 hours' stirring at 72° C., a further 2.5 g (0.015 mol) of 4-aminobenzoic acid ethyl ester are added. After a further one hour's stirring at 72° C., the mixture is allowed to cool. After being left to stand overnight, the reaction mixture is heated to 50° C. and filtered through a suction filter. The filter cake is washed with 5% NaCl solution, taken up in 2 liters of ethanol and stirred for 2 h. After leaving to stand overnight, the precipitate is filtered off, washed with ethanol and acetone and dried in vacuo at 80° C., yielding 305.4 g (97.24%) of yellow crystals of the intermediate (100a), which discolour in air.

(b) Compound of Formula (100)

32.0 g (0.31 mol) of 3-dimethylamino-1-propylamine are introduced into a 350 ml sulfonation flask equipped with a condenser and pH meter. At 50° C., 19.34 g (0.02 mol) of the intermediate of formula (100a) are introduced. The mixture is then stirred for 3 h at 50–55° C., during which time the yellow suspension becomes a solution. The mixture is then heated for 3 h at 60° C. The mixture is then heated to 70° C. and stirred for 1.5 h. After being cooled to RT (room temperature), the mixture is diluted with 25 ml of water, and the clear solution is left to stand overnight. The solution is then diluted with water and adjusted to pH 1 with conc. hydrochloric acid. The precipitate is filtered off with suction, taken up in 5% NaCl solution, filtered again at pH 4 and washed with 5% NaCl solution and then dried in vacuo at 70° C.

Yield: 21.6 g

I.2. Compound of Formula (101)

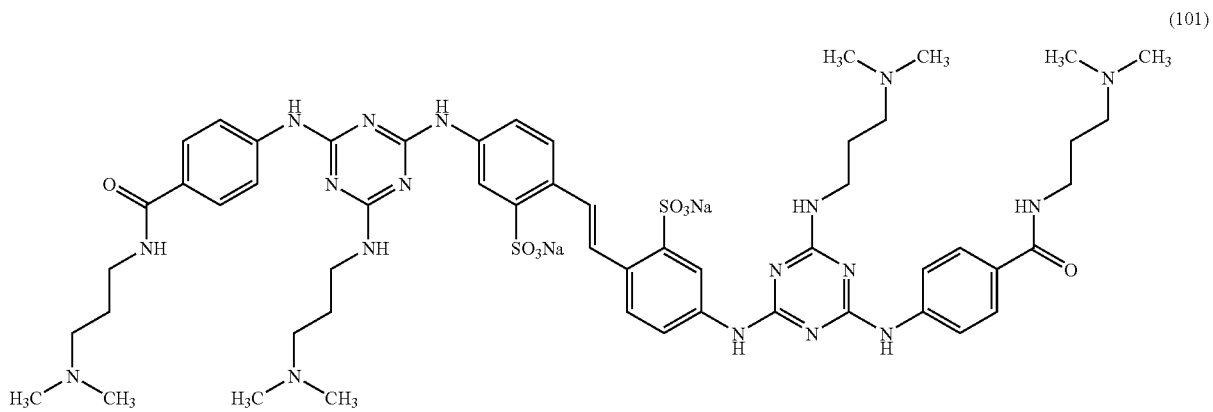

32.0 g (0.31 mol) of 3-dimethylamino-1-propylamine are introduced into a 100 ml sulfonation flask equipped with a condenser. At 60° C., 19.3 g (0.02 mol) of the intermediate of formula (100a) are introduced. The mixture is boiled under reflux (122–125° C.) for 24 h. After cooling to RT, the crude product is diluted with water and concentrated using a rotary evaporator. That process is repeated twice. The pH is then adjusted to 8.0 and the supernatant solution is poured off. The residue is suspended in 5% NaCl solution and acetone and stirred for 1 h. The precipitate is filtered off with suction, again taken up in acetone, filtered and washed with acetone. The crystals so obtained are dried in vacuo at 70° C.

Yield: 20.2 g (87%)

I.3. Compound of Formula (102)

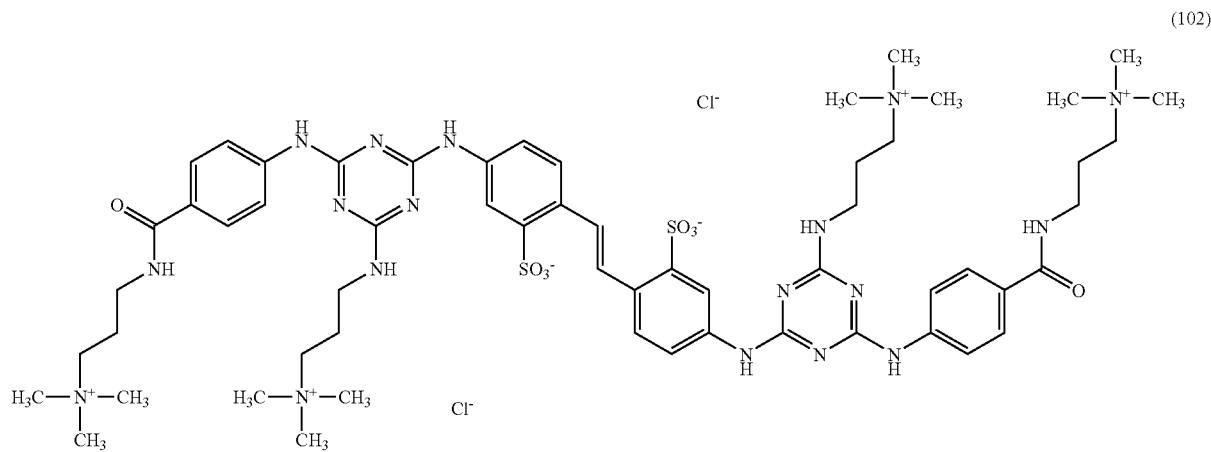

50 ml of water and 40 ml of 2N NaOH are heated at 70° C. in a 350 ml sulfonation flask. 10.0 g (8 mmol) of the compound of formula (101) prepared according to Example I.2 are added, there being formed initially a yellow solution, then a two-phase mixture. After cooling to 40° C., 8.0 g (0.064 mol) of dimethyl sulfate are added dropwise. The mixture is stirred for 2 h at 50° C.; then 10 ml of 2N NaOH and 2.0 g (0.016 mmol) of dimethyl sulfate are added. After being stirred for a further 2.5 h at 50° C., the mixture is heated to 75° C. in order to destroy excess dimethyl sulfate. After cooling to RT and leaving to stand overnight, the supernatant solution is poured off, and the residue is suspended in 10% NaCl solution. The pH is adjusted to 8–9, the supernatant solution is poured off and the residue is again suspended in 10% NaCl solution. The solid is separated off in a centrifuge and dried in vacuo at 70° C.

Yield: 9.4 g (90%).

I.4. Compound of Formula (103)

20 g (0.327 mol) of ethanolamine are heated at 50° C. in a 100 ml sulfonation flask equipped with a condenser and pH meter. 10.5 g (0.01 mol) of the compound of formula (100) prepared according to Example I.1 are introduced in very small portions. The mixture is stirred for 5 h at 120° C. and left to stand overnight. After addition of 50 ml of water, firstly a yellow solution and after a few minutes a two-phase mixture is obtained. The water is poured off and the residue is again suspended in water at pH 6. The yellow precipitate is filtered off and washed with 5% NaCl solution. The residue is taken up in 5% NaCl solution and stirred at pH 6.0–6.5. The yellow crystals are filtered off, washed again with 5% NaCl solution and dried in vacuo at 70° C.

Yield: 7.7 g (71%)

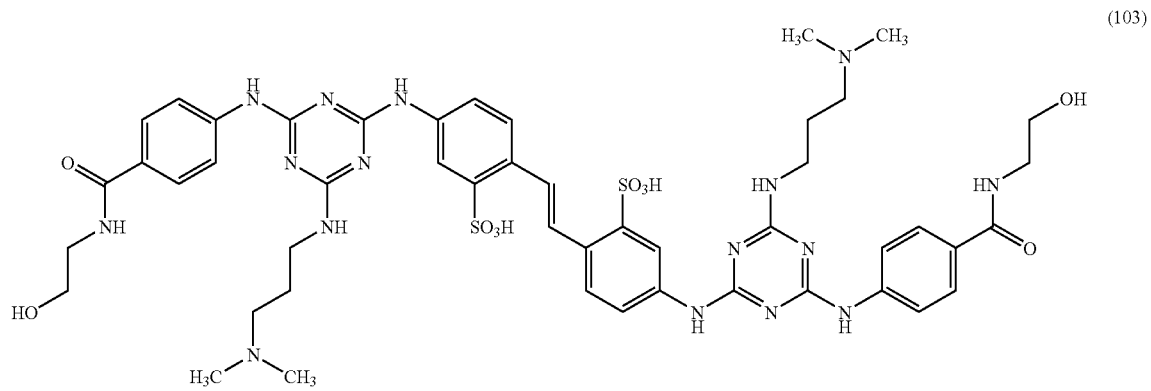

I.5. Compound of Formula (104)

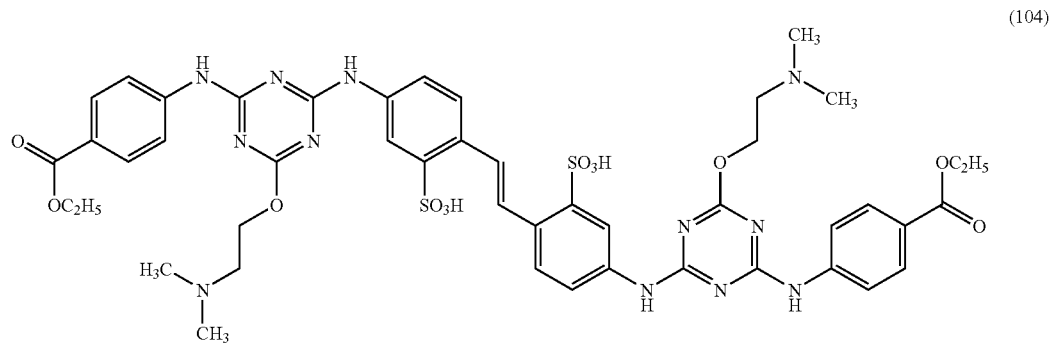

In a 350 ml sulfonation flask equipped with a condenser and pH meter, 75 g (0.84 mol) of 2-dimethylaminoethanol are heated at 45° C. 21.7 g (0.022 mol) of intermediate of formula (100a), prepared according to Example I.1, are introduced and the mixture is stirred for 1 h at 70° C. After being cooled to RT, the reaction mixture is poured into 300 ml of acetone. The light-yellow supernatant solution is poured off and the residue is again taken up in 300 ml of acetone. The now colourless supernatant solution is decanted off, and the residue is filtered, washed with acetone and suspended in 250 ml of water. After 30 minutes' stirring at pH 5.5, the light-yellow crystals are filtered off, washed with water and dried in vacuo at 70° C.

Yield: 19.0 g (84%)

I.6. Compound of Formula (105)

200 g of ice-water and 60 g (0.325 mol) of cyanuric chloride dissolved in 465 ml of methyl ethyl ketone are introduced into a 2.5 liter flat-flanged flask. Then, in the course of 40 min, 493 ml of a 12% solution of 4,4'-diaminostilbene-2,2'-disulfonic acid in soda water are slowly added dropwise at pH 4.5–5.0 so that no excess of disulfonic acid is formed. When the addition is complete, stirring is carried out for 10 min at an internal temperature of 5–10° C. Using a metering pump, the suspension so obtained is added dropwise in the course of 35 min at 55–60° C. and pH 7.0–7.5 to a solution of 61.5 g (0.341 mol) of 4-amino-N-(2-hydroxyethyl)benzamide in 450 ml of water. The mixture is then stirred for 1 h at 60° C. and the methyl ethyl ketone is distilled off at 90° C. After cooling to 70° C.,

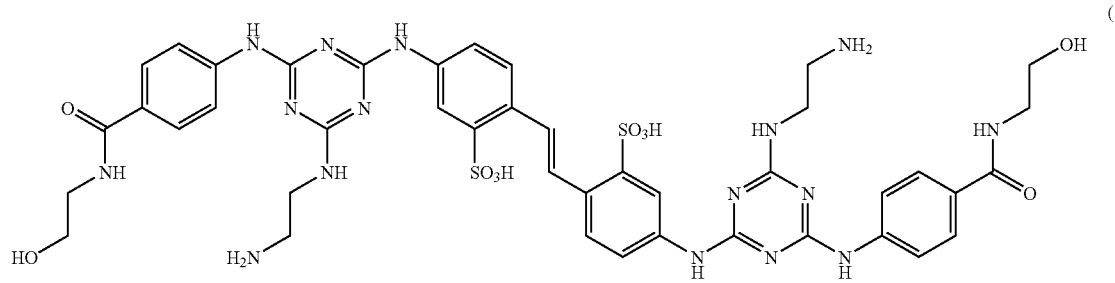

(a) Intermediate of Formula (105a)

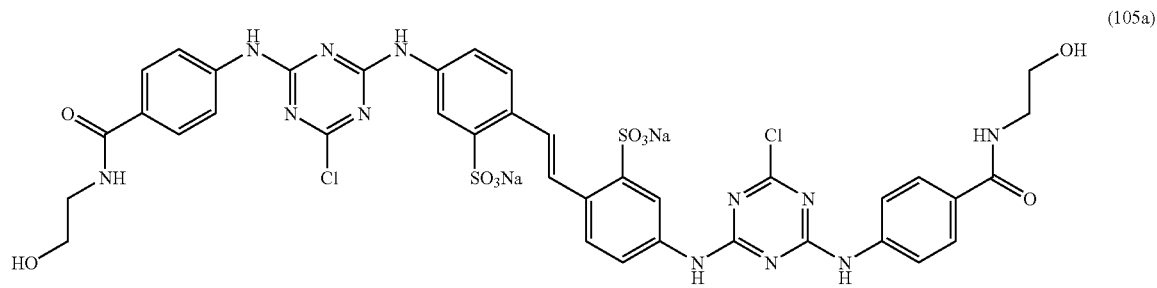

the yellow crystals are filtered through a suction filter, washed with 2.5% NaCl solution and dried in vacuo at 70° C.

Yield: 144.6 g (b) Compound of Formula (105)

25.3 g (0.42 mol) of ethylenediamine in 150 ml water and 150 ml dioxane are introduced into a 750 ml sulfonation flask equipped with a condenser and pH meter. At 70–75° C., 35.0 g (0.035 mol) of the intermediate of formula (105a) are introduced. The yellow solution is stirred for 1 h at 86–88° C. After being cooled to 70° C., the solution is then diluted with 100 ml of water and adjusted to pH 4.0 with 75 ml of conc. hydrochloric acid. Stirring is continued for a further 1 h at 70° C. The precipitate is filtered through a suction filter and washed with a small amount of water. The filter cake is again suspended in 500 ml of water and dissolved at 70° C. and pH 10.9. The pH is then adjusted to 3.5 with conc. hydrochloric acid. The yellow crystals are filtered through a suction filter, washed three times with 5% NaCl solution and dried in vacuo at 70° C.

Yield: 36.7 g

I.7. Compound of Formula (106)

36.2 g (0.35 mol) of diethylenetriamine in 150 ml water and 150 ml of dioxane are introduced into a 750 ml sulfonation flask equipped with a condenser and pH meter. At 70–75° C., 35.0 g (0.035 mol) of the intermediate of formula (105a) prepared according to Example I.6 are introduced. The yellow solution is stirred for 3.5 h at 86–88° C. After cooling to 70° C., the solution is then diluted with 100 ml of of water and adjusted to pH 4.5 with 115 ml of conc. hydrochloric acid. After being cooled to RT, the mixture is stirred for a further 1 h. The precipitate is filtered through a suction filter and washed three times with 2.5% NaCl solution. The filter cake is again suspended in 500 ml of water. After adjustment to pH 5.3, the yellow crystals are filtered through a suction filter, washed with 2.5% NaCl solution and dried in vacuo at 70° C.

Yield: 32.8 g (81%)

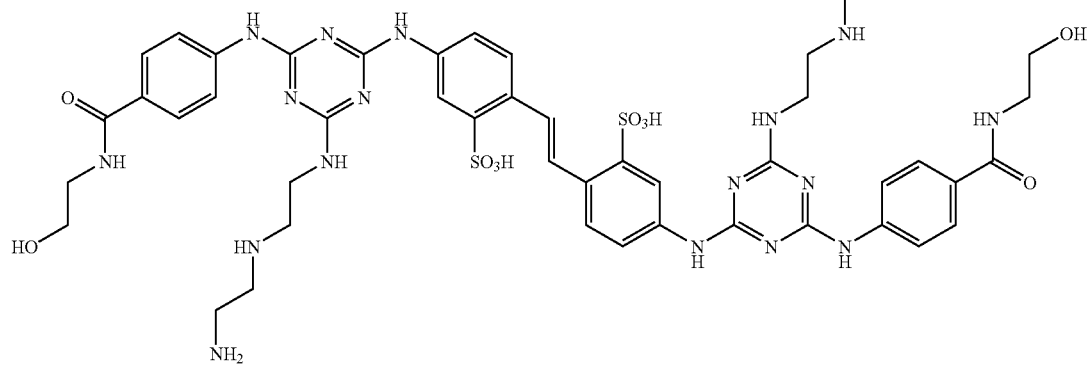

I.8. Compound of Formula (107)

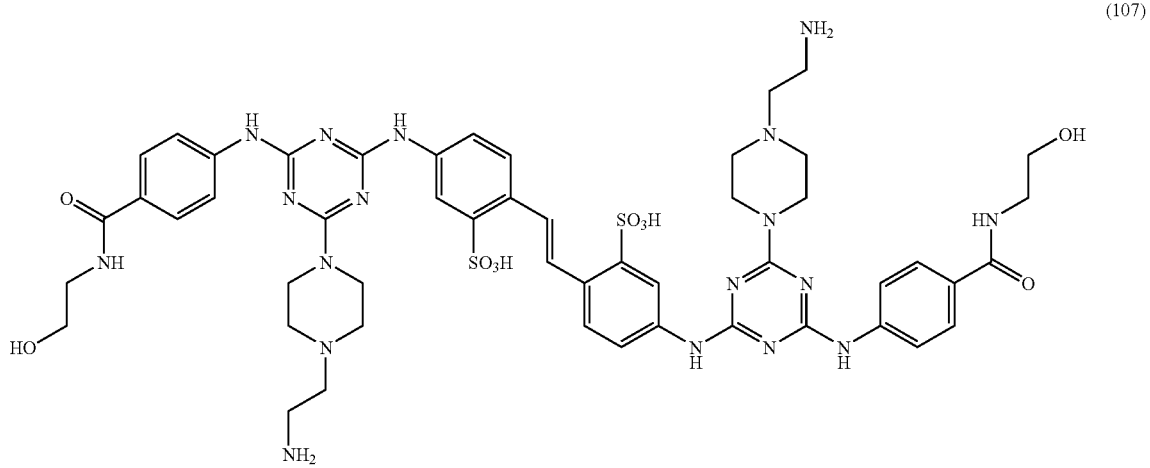

43.0 g (0.33 mol) of 1-(2-aminoethyl)-piperazine in 150 ml of water and 150 ml of dioxane are introduced into a 750 ml sulfonation flask equipped with a condenser and pH meter. At 70–75° C., 35.0 g (0.035 mol) of the intermediate of formula (105a) prepared according to Example I.6 are introduced. The yellow solution is stirred for 2 h at 86–88° C. After being cooled to 70° C., the solution is then diluted with 100 ml of water and adjusted to pH 4.0 with 65 ml of conc. hydrochloric acid. After being cooled to RT, the mixture is stirred for a further 1 h. The precipitate is filtered through a suction filter and washed with water. The filter cake is again suspended in 120 ml of water and 50 ml of 5% NaCl solution. After adjustment to pH 5.0–5.5, the mixture is stirred for a further 4 h. The yellow crystals are then filtered through a suction filter, washed with 5% NaCl solution and dried in vacuo at 70° C.

Yield: 42.9 g

I.9. Compound of Formula (108)

19.1 g (0.15 mol) of 1-(2-hydroxyethyl)-piperazine in 100 ml of water and 100 ml of dioxane are introduced into a 350 ml sulfonation flask equipped with a condenser and pH meter. At 70–75° C., 35.0 g (0.025 mol) of the intermediate of formula (105a) prepared according to Example I.6 are introduced. The yellow solution is stirred for 3 h at 86–88° C. After being cooled to 70° C., the solution is then diluted with 50 ml of water and adjusted to pH 5.0 with 15 ml of conc. hydrochloric acid. After cooling to RT, the precipitate is filtered through a suction filter and washed with water. The filter cake is again suspended in 250 ml of water. After adjustment to pH 5, the mixture is stirred for a further 1 h at 70° C. The yellow crystals are then filtered through a suction filter, washed with water and dried in vacuo at 70° C.

Yield: 25.8 g (90%)

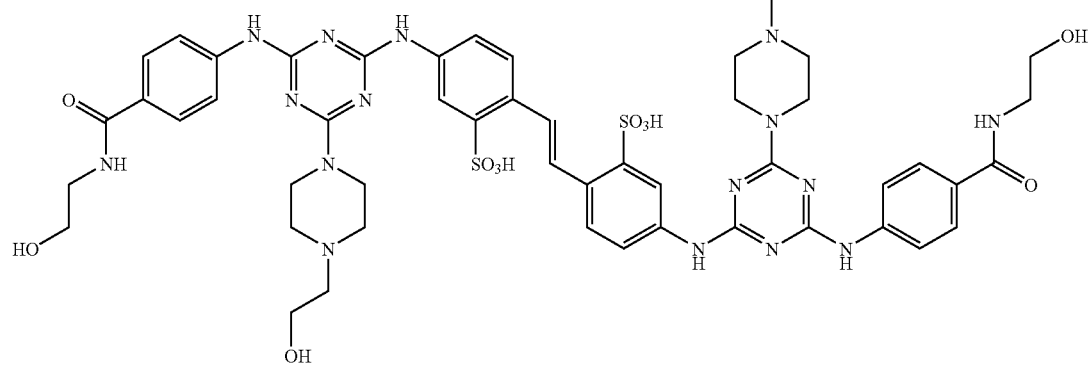

(108)

I.10. Compound of Formula (109)

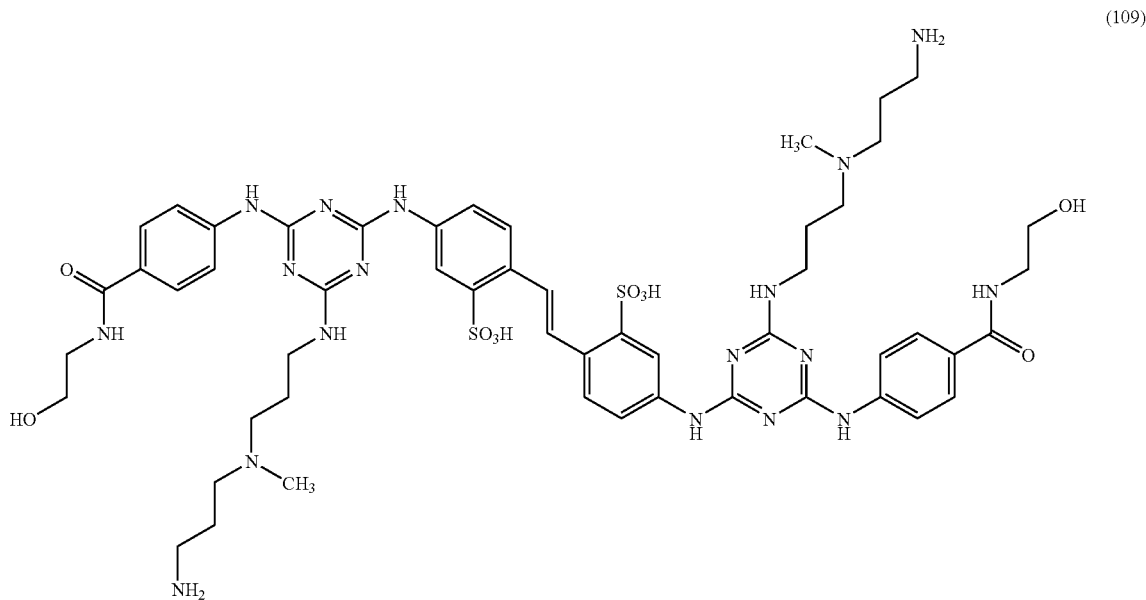

(109)

18.8 g (0.13 mol) of N,N-bis(3-aminopropyl)methylamine in 100 ml of water and 100 ml of dioxane are introduced into a 350 ml sulfonation flask equipped with a condenser and pH meter. At 70–75° C., 22.7 g (0.021 mol) of the intermediate of formula (105a) prepared according to Example I.6 are introduced. The yellow solution is stirred for 3 h at 86–88° C. After cooling to 70° C., the solution is then diluted with 120 ml of water and adjusted to pH 4.5 with 35 ml of conc. hydrochloric acid. After addition of 100 ml of acetone, the precipitate is filtered through a suction filter, washed with water and dried in vacuo at 70° C.

Yield: 28.7 g

I.11. Compound of Formula (110)

C. After being cooled to 70° C., the solution is adjusted to pH 4.5 with 10 ml of conc. hydrochloric acid. After being cooled to RT, the mixture is stirred for a further 1 h. The precipitate is filtered through a suction filter and washed three times with water. The filter cake is again suspended in 300 ml of water and the mixture is stirred at pH 5 for a further 1 h. The yellow crystals are then filtered through a suction filter, washed with water and dried in vacuo at 70° C.

Yield: 25.2 g (90%)

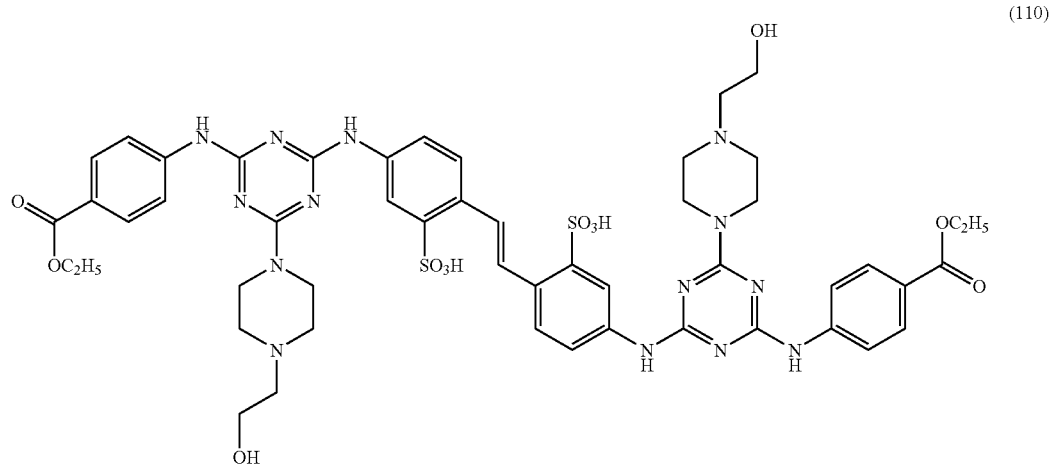

I.12. Compound of Formula (111)

7.9 g (0.059 mol) of 1-(2-hydroxyethyl)-piperazine in 120 ml of water and 120 ml of dioxane are introduced into a 750 ml sulfonation flask equipped with a condenser and pH meter. At 70–75° C., 25.0 g (0.025 mol) of the intermediate of formula (100a) prepared according to Example I.1 are introduced. The yellow solution is stirred for 3 h at 86–88°

9.1 g (0.15 mol) of ethylenediamine in 120 ml of water and 120 ml of dioxane are introduced into a 750 ml sulfonation flask equipped with a condenser and pH meter. At 70–75° C., 25.4 g (0.025 mol) of the intermediate of formula (100a) prepared according to Example I.1 are introduced. The yellow solution is stirred for 4 h at 86–88°

C. After being cooled to 70° C., the solution is adjusted to pH 4.5 with 18 ml of conc. hydrochloric acid and left to stand overnight. After the supernatant solution has been poured off, the residue is triturated in a mortar, filtered through a suction filter, washed with water and dried in vacuo at 70° C.

Yield: 22.6 g (93%)

I.13. Compound of Formula (112)

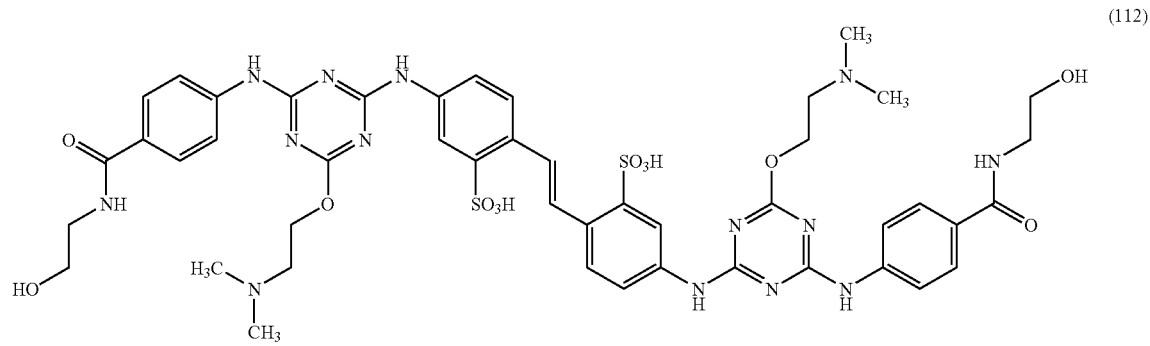

(112)

100 ml (1 mol) of 2-dimethylaminoethanol are introduced into a 350 ml sulfonation flask equipped with a condenser and pH meter. At 70–75° C., 30.0 g (0.03 mol) of the intermediate of formula (105a) are introduced. The yellow suspension is stirred for 1 h at 110–115° C. After being cooled to 90° C., the mixture is then diluted with 100 ml of water. The solution is concentrated using a rotary evaporator, and the residue is dissolved in 150 ml of water. The pH is adjusted to 4.5 by addition of 20 ml of conc. hydrochloric acid. The precipitate is filtered through a suction filter, washed with water and dried in vacuo at 80° C.

Yield: 21.8 g (68%)

I.14. Compound of Formula (113)

5.9 g (0.045 mol) of 3-diethylaminopropylamine in 70 ml of water are introduced into a 350 ml sulfonation flask equipped with a condenser and pH meter. At 70–75° C., 15.7 g (0.015 mol) of the intermediate of formula (105a) are introduced. The mixture is stirred for 4 h at 96–98° C. and after cooling to 70° C. is diluted with 100 ml of water. The pH is adjusted to 2.0 by addition of 7 ml of conc. hydrochloric add. The precipitate is filtered through a suction filter and washed with a small amount of water. The filter cake is then suspended in 450 ml of water and stirred for 2 h at RT. The precipitate is filtered through a suction filter, washed with 2.5% NaCl solution and dried in vacuo at 70° C.

Yield: 16.8 g (98%)

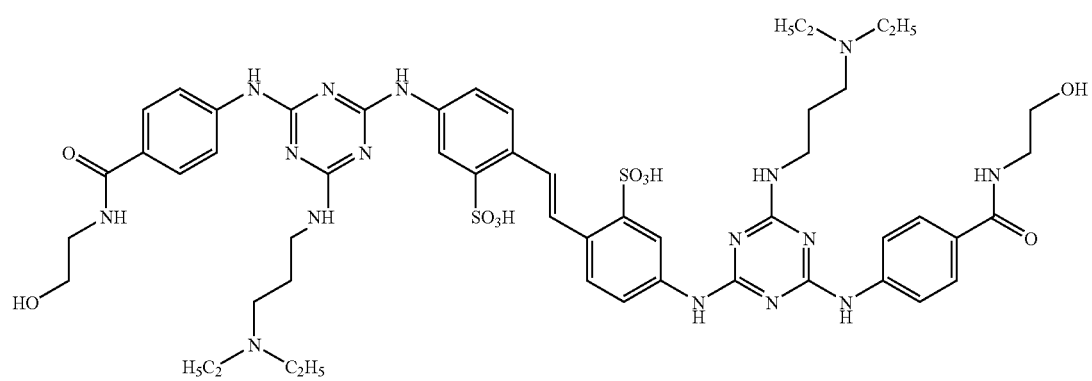

(113)

I.15. Compound of Formula (114)

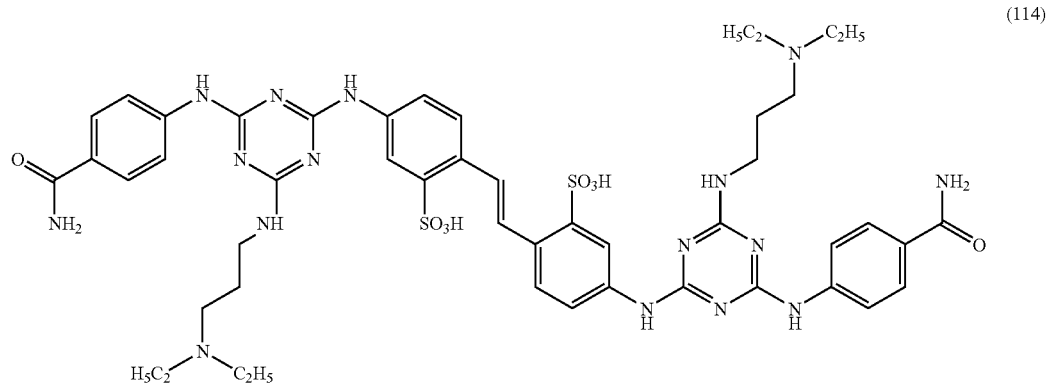

(a) Intermediate of Formula (114a)

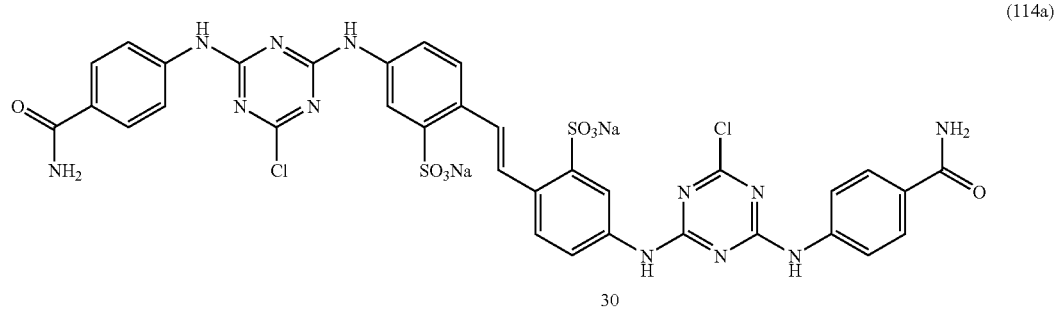

400 g of ice-water and 120 g (0.65 mol) of cyanuric chloride dissolved in 753 g of methyl ethyl ketone are introduced into a 2.5 liter flat-flanged flask equipped with a condenser, stirrer and pH meter. Then, in the course of 65 min, 990 ml of a 12% solution of 4,4'-diaminostilbene-2,2'-disulfonic acid in soda water are slowly added dropwise at pH 4.5–5.0 so that no excess of disulfonic acid is formed. When the addition is complete, stirring is carried out for a further 10 min at an internal temperature of 5–10° C. Then, in the course of 15 min, 90.3 g (0.65 mol) of 4-aminobenzamide are introduced at 10–20° C. and pH 7.0–7.5 into the resulting yellow suspension. The yellow suspension is then heated to 72° C. in the course of one hour and stirred at that temperature for a further 2 h. After the solvent has been distilled off, the mixture is stirred for 4 h at 85° C. and then left to stand overnight at RT. The crude product is filtered through a suction filter, washed with water and dried in vacuo at 80° C.

Yield: 327 g Appearance: yellow crystals (b) Compound of Formula (114)

130 ml of water are introduced into a 350 ml sulfonation flask equipped with a condenser and pH meter and, at 70–75° C., 30.0 g (0.033 mol) of the intermediate of formula (114a) are introduced. 13.0 g (0.098 mol) of 1-amino-3-diethylaminopropane are then added dropwise. The yellow suspension so obtained is stirred for 8 h at 96–97° C. and then left to stand overnight at RT. The pH is adjusted to 4.5 by addition of 12 ml of conc. hydrochloric acid. The precipitate is filtered through a suction filter, washed with 200 ml of water and then dried in vacuo at 80° C.

Yield: 30.0 g (86%) Appearance: beige crystals

I.16. Compound of Formula (115)

(a) Intermediate of Formula (115a)

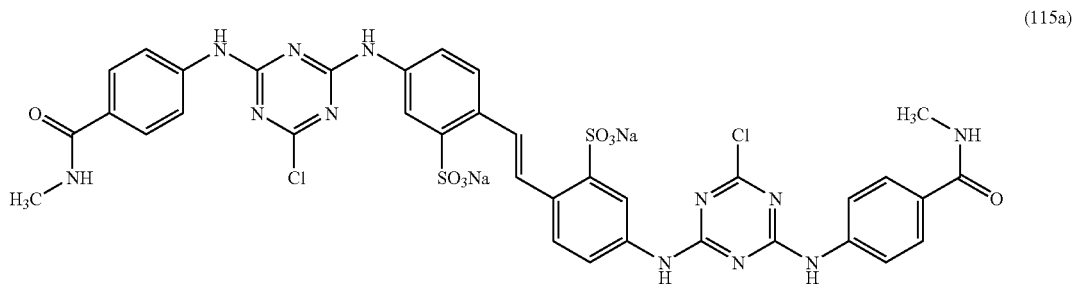
(115a)

400 g of ice-water and 120 g (0.65 mol) of cyanuric chloride dissolved in 753 g of methyl ethyl ketone are introduced into a 2.5 liter flat-flanged flask equipped with a condenser, stirrer and pH meter. Then, in the course of 65 min, 977 ml of a 12% solution of 4,4'-diaminostilbene-2,2'-disulfonic acid in soda water are slowly added dropwise at pH 4.5–5.0 so that no excess of disulfonic acid is formed. When the addition is complete, stirring is carried out at an internal temperature of 5–10° C. for a further 10 min. Then, in the course of 15 min, 97.6 g (0.65 mol) of 4-amino-N-methylbenzamide are introduced at 10–20° C. and pH 7.0–7.5 into the resulting yellow suspension. The yellow suspension is then heated to 72° C. in the course of one hour and stirred at that temperature for a further 2 h. After the solvent has been distilled off, a further 200 ml of water are added and the mixture is stirred for a further 1.5 h at 85° C. After cooling to 75° C., the crude product is filtered through a suction filter, washed with 2.5% NaCl solution and dried in vacuo at 80° C.

Yield: 306.1 g Appearance: yellow crystals (b) Compound of Formula (115)

130 ml of of water are introduced into a 350 ml sulfonation flask equipped with a condenser and pH meter and, at 70° C., 30.0 g (0.030 mol) of the intermediate of formula (115a) are introduced. 12.1 g (0.091 mol) of 1-amino-3-diethylaminopropane are then added dropwise. The yellow suspension so obtained is stirred for 4 h at 96–97° C. After cooling to 70° C., the pH is adjusted to 4.5 by addition of 8 ml of conc. hydrochloric acid. The precipitate is filtered off through a suction filter, washed with 200 ml of water and then dried in vacuo at 80° C.

Yield: 32.5 g (100%) Appearance: yellow crystals

What is claimed is:

1. A compound of formula (1), (2) or (3)

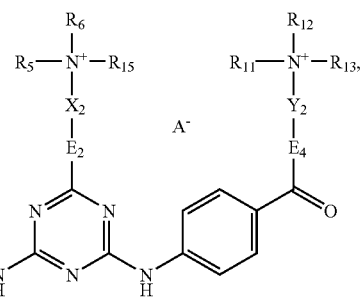

-continued

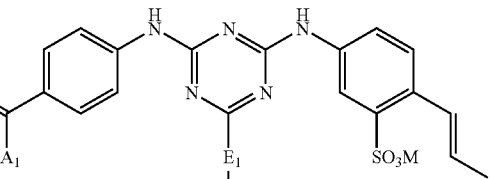

(2)

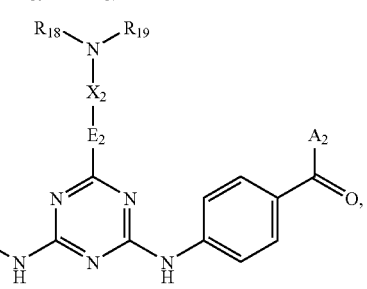

(3)

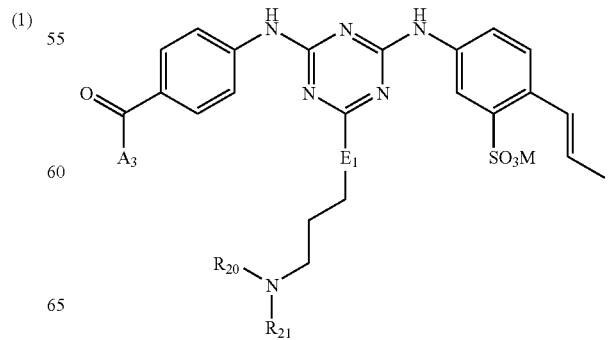

-continued

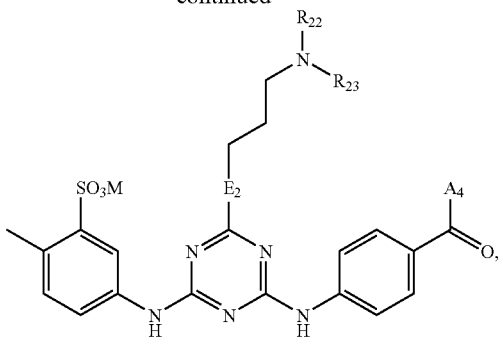

wherein

M is hydrogen, an alkali metal ion or an ammonium ion, $A_1$ is —$OR_1$, —$NHR_1$, N-morpholinyl or 1-piperidyl, $A_2$ is —$OR_2$, —$NHR_2$, N-morpholinyl or 1-piperidyl, $E_1$, $E_2$, $E_3$ and $E_4$ are each independently of the others —O—, —NH— or —$NR_9$—, wherein $R_9$ together with $R_4$, $R_6$, $R_2$ or $R_{12}$ forms an ethylene radical, $R_1$ to $R_6$, $R_{11}$ and $R_{12}$ are each independently of the others hydrogen, alkyl, alkoxy, aryl, aralkyl, alkoxyalkyl, hydroxyalkyl, aminoalkyl or a group of the formula —$(C_nH_{2n}Y)_m$—$R_7$, wherein Y is —O—, —NH—, —$NR_8$—, —CONH— or —$CONR_8$—, $R_7$ is hydrogen, alkyl or aryl and $R_8$ is alkyl or aryl, n is a number from 2 to 6 and m is a number from 1 to 10, or pairs of two radicals $R_1$ and $R_2$, $R_3$ and $R_4$, $R_5$ and $R_6$ or $R_{11}$ and $R_{12}$ together form a bivalent radical of the formula —$CH_2CH_2OCH_2CH_2$— or, when $E_1$, $E_2$, $E_3$ or $E_4$ is —$NR_9$—, $R_4$, $R_6$, $R_2$ or $R_{12}$ together with $R_9$ forms an ethylene radical, $R_{10}$, $R_{13}$, $R_{14}$ and $R_{15}$ are each independently of the others alkyl, alkenyl, aryl or aralkyl, $X_1$ and $X_2$ are each independently of the other 1,2-cyclohexanediyl, a group of the formula —$(C_nH_{2n})_m$— or a group of the formula —$(C_nH_{2n}Y)_m$—, wherein Y is —O—, —NH—, —$NR_8$—, —CONH— or —$CONR_8$— and $R_8$ is alkyl or aryl, n is a number from 2 to 6 and m is a number from 1 to 10, $Y_1$ and $Y_2$ are each independently of the other 1,2-cyclohexanediyl, a group of the formula —$(C_nH_{2n})_m$— or a group of the formula —$(C_nH_{2n}Y)_m$—, wherein Y is —O—, —NH—, —$NR_8$—, —CONH— or —$CONR_8$— and $R_8$ is alkyl or aryl, n is a number from 2 to 6 and m is a number from 1 to 10 and $A^-$ is a singly charged anion or the two $A^-$ form a doubly charged anion, $R_{16}$, $R_{17}$, $R_{18}$ and $R_{19}$ are each independently of the others hydrogen, 2-hydroxyethyl, 2-aminoethyl or 3-aminopropyl, $R_{20}$, $R_{21}$, $R_{22}$ and $R_{23}$ are each independently of the others alkyl, and $A_3$ and $A_4$ are 2-hydroxyethylamino, 3-dimethylaminopropylamino or 3-diethylaminopropylamino.

2. A compound of formula (2) or (3) according to claim 1, wherein the substituents $A_1$ and $A_2$, $A_3$ and $A_4$, $E_1$ and $E_2$, $X_1$ and $X_2$, $R_{16}$ and $R_{18}$, $R_{17}$ and $R_{19}$, $R_{20}$ and $R_{22}$ and also $R_{21}$ and $R_{23}$ are in each case identical.

3. A compound of formula (1) according to claim 1, wherein the substituents $E_1$ and $E_2$, $E_3$ and $E_4$, $X_1$ and $X_2$, $Y_1$ and $Y_2$, $R_3$ and $R_5$, $R_4$ and $R_6$, $R_{14}$ and $R_{15}$, $R_1$ and $R_{11}$, $R_2$ and $R_{12}$ and also $R_{10}$ and $R_{13}$ are in each case identical.

4. A compound of formula (1) or (2) according to claim 1, wherein $X_1$ and $X_2$ are ethylene or trimethylene.

5. A compound of formula (3) according to claim 1, wherein $R_{20}$, $R_{21}$, $R_{22}$ and $R_{23}$ are methyl or ethyl.

6. A compound of formula (2) or (3) according to claim 1, wherein $A_1$, $A_2$, $A_3$ and $A_4$ are amino, methylamino, 2-hydroxyethylamino, 3-dimethylaminopropylamino or ethoxy.

7. A compound of formula (1) according to claim 1, wherein $R_1$ to $R_6$ and $R_{10}$ to $R_{15}$ are methyl.

8. A process for the preparation of a compound of formula (2) according to claim 1 wherein the substituents $A_1$ and $A_2$, $A_3$ and $A_4$, $E_1$ and $E_2$, $X_1$ and $X_2$, $R_{16}$ and $R_{18}$, $R_{17}$ and $R_{19}$, $R_{20}$ and $R_{22}$ and also $R_{21}$ and $R_{23}$ are in each case identical, which process comprises reacting cyanuric chloride by known methods with, in succession in any order, a compound of formula (4)

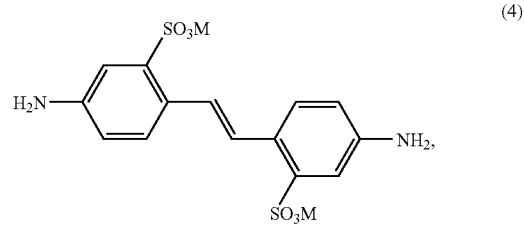

a compound of formula (5)

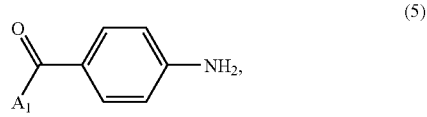

and a compound of formula (6)

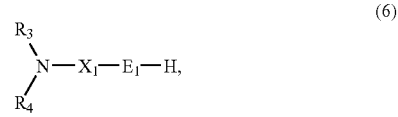

wherein M, $A_1$, $E_1$, $X_1$, $R_3$ and $R_4$ are as defined in claim 1.

9. A process for the preparation of a compound of formula (3) according to claim 1 wherein the substituents $A_1$ and $A_2$, $A_3$ and $A_4$, $E_1$ and $E_2$, $X_1$ and $X_2$, $R_{16}$ and $R_{18}$, $R_{17}$ and $R_{19}$, $R_{20}$ and $R_{22}$ and also $R_{21}$ and $R_{23}$ are in each case identical, which process comprises reacting cyanuric chloride by known methods with, in succession in any order, a compound of formula (4)

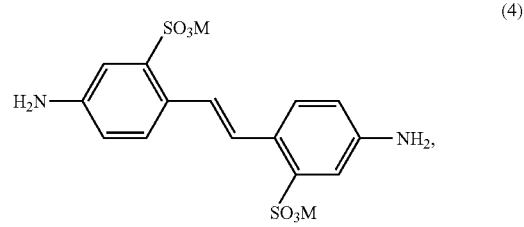

a compound of formula (7)

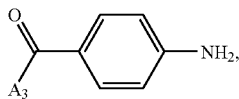

and a compound of formula (8)

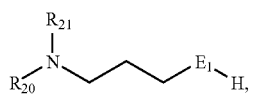

wherein M, $A_3$, $E_1$, $R_{20}$ and $R_{21}$ are as defined in claim 1.

10. A method for the optical brightening of natural, semi-synthetic or synthetic textile fibres, which comprises treating said fibres in an aqueous medium with an effective amount of a compound of formula (1), (2) or (3) according to claim 1.

11. A method for the optical brightening of paper, which comprises treating said paper fibres in an aqueous medium with an effective amount of a compound of formula (1), (2) or (3) according to claim 1.

12. A method of increasing the SPF of a textile fibre material, comprising the treatment of the textile fibre material with 0.05–3.0% by weight, based on the weight of the textile fibre material, of one or more compounds of formula (1), (2) or (3) according to claim 1.

13. A composition for brightening synthetic or natural organic materials, comprising water, a compound of formula (1), (2) or (3) according to claim 1 and optionally further adjuvants.

* * * * *